US009423334B2

(12) United States Patent
Anderson

(10) Patent No.: US 9,423,334 B2
(45) Date of Patent: Aug. 23, 2016

(54) METHOD OF CAVITATION/FLASHING DETECTION IN OR NEAR A PROCESS CONTROL VALVE

(71) Applicant: FISHER CONTROLS INTERNATIONAL LLC, Marshalltown, IA (US)

(72) Inventor: Shawn W. Anderson, Haverhill, IA (US)

(73) Assignee: FISHER CONTROLS INTERNATIONAL LLC, Marshalltown, IA (US)

( * ) Notice: Subject to any disclaimer, the term of this patent is extended or adjusted under 35 U.S.C. 154(b) by 235 days.

(21) Appl. No.: 14/011,469

(22) Filed: Aug. 27, 2013

(65) Prior Publication Data

US 2015/0059886 A1    Mar. 5, 2015

(51) Int. Cl.

| | |
|---|---|
| *G01N 29/14* | (2006.01) |
| *G01N 13/00* | (2006.01) |
| *F16K 51/00* | (2006.01) |
| *G01N 29/02* | (2006.01) |
| *G01N 29/44* | (2006.01) |
| *F16K 37/00* | (2006.01) |

(52) U.S. Cl.
CPC ............ *G01N 13/00* (2013.01); *F16K 37/0083* (2013.01); *F16K 37/0091* (2013.01); *F16K 51/00* (2013.01); *G01N 29/02* (2013.01);
(Continued)

(58) Field of Classification Search
CPC .. G01N 13/00; G01N 29/14; G01N 29/4409; G01N 29/02; G01N 2291/044; G01N 2291/022; F16K 37/0091; F16K 37/0083; F16K 51/00; Y10T 137/8158

USPC ................................................... 73/581, 692
See application file for complete search history.

(56) References Cited

U.S. PATENT DOCUMENTS 4,565,964 A * 1/1986 Matthews et al. ............ 324/539
5,176,032 A * 1/1993 Holroyd et al. ................ 73/587
(Continued)

FOREIGN PATENT DOCUMENTS

| EP | 2423429 A1 | 2/2012 |
|---|---|---|
| WO | WO-95/06276 A1 | 3/1995 |

OTHER PUBLICATIONS

International Search Report and Written Opinion from International Application No. PCT/US2014/052798 dated Jan. 22, 2015.
(Continued)

*Primary Examiner* — Daniel S Larkin
*Assistant Examiner* — Rose M Miller
(74) *Attorney, Agent, or Firm* — Marshall, Gerstein & Borun LLP

(57) ABSTRACT

A system and apparatus for detecting and monitoring cavitation inside a flow control device, such as a control valve, includes an acoustic emission sensor coupled to the flow control device in a manner to acquire acoustic signals caused by cavitation. A processor receives acoustic information from the acoustic emission sensor. The processor selectively identifies cavitation events from the acoustic information that meet certain predefined criteria. Cavitation levels are monitored based on at least one of a rate of cavitation events and intensity of individual cavitation events. The cavitation levels may be used to identify the presence of cavitation in the flow control device, to track accumulated cavitation in the flow control device, and/or to identify significant changes in the cavitation levels over time. This information may be used to reduce cavitation, estimate repair and maintenance, and/or monitor performance of the flow control device.

24 Claims, 6 Drawing Sheets

(52) U.S. Cl.
CPC .......... *G01N29/14* (2013.01); *G01N 29/4409* (2013.01); *G01N 2291/022* (2013.01); *G01N 2291/044* (2013.01); *Y10T 137/8158* (2015.04)

(56) References Cited

U.S. PATENT DOCUMENTS

| | | |
|---|---|---|
| 5,650,943 A | 7/1997 | Powell et al. |
| 6,954,713 B2 | 10/2005 | Eryurek |
| 7,290,450 B2 | 11/2007 | Brown et al. |
| 7,814,936 B2 | 10/2010 | Catron |
| 2003/0019297 A1 | 1/2003 | Fiebelkorn et al. |
| 2007/0068225 A1 | 3/2007 | Brown |
| 2010/0192677 A1 | 8/2010 | Puttmer |
| 2010/0300683 A1 | 12/2010 | Looper et al. |

OTHER PUBLICATIONS

International Preliminary Report on Patentability from International Application No. PCT/US2014/052798, dated Mar. 10, 2016.

\* cited by examiner

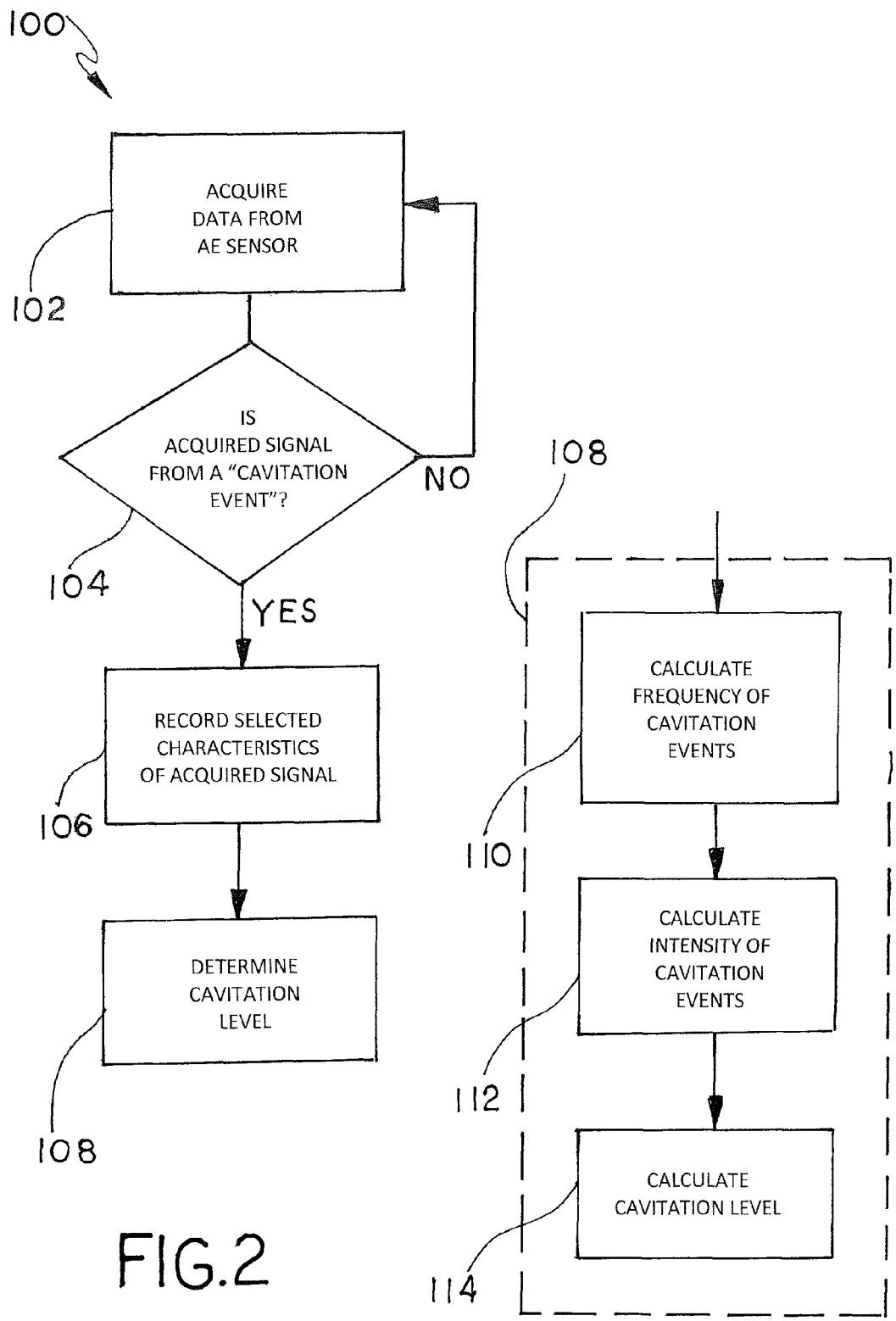

METHOD OF CAVITATION/FLASHING DETECTION IN OR NEAR A PROCESS CONTROL VALVE

FIELD OF THE INVENTION

The present invention relates to methods of and apparatus for detecting and monitoring cavitation in liquids in or near a flow control device, such as a control valve or pipe.

BACKGROUND

Cavitation within a stream of liquid occurs when the fluid pressure of the liquid drops below its vapor pressure in a controlled flow stream of fluid, such as in a pipe or control valve, and gas bubbles are formed in the flow stream. Subsequently, when the fluid pressure recovers to a level above the vapor pressure, the gas bubbles collapse and implode violently in a process that produces a significant high energy acoustic wave. Sometimes, the formation of the initial gas bubbles is referred to as "flashing," whereas the implosion of the gas bubbles is referred to as "cavitation." For purposes of this description, however, the term "cavitation" is hereafter used to encompass the overall process of both the formation and the implosion of the gas bubbles unless clearly indicated otherwise.

Control valves often have at least one region of reduced flow area somewhere between an inlet into the valve body and an outlet from the valve body. One typical region of reduced flow area is at or near the orifice defined by the valve seat and/or proximate the valve trim. Therefore, fluid flowing through a control valve usually experiences some level of pressure drop or pressure loss as it travels through the reduced flow area. The pressure will typically have a lowest value somewhere inside or immediately downstream of the control valve body before increasing somewhat. In some circumstances, these lower pressure conditions can cause cavitation in the control valve between the valve trim and the outlet and/or in the pipe immediately adjacent the outlet.

Cavitation within the stream of liquid passing through the control valve can be problematic. Cavitation inside or near the physical boundaries of the control valve can cause severe physical damage to the control valve or the adjacent piping components. For example, cavitation at or near the inner wall surface of the flow channel through the valve body or the valve trim may cause damage to the pressure boundary, the valve trim, or other valve components. The damage typically accumulates over time such that periodic maintenance must be performed on the control valve to repair damage to components caused by the cavitation. When scheduling maintenance on many industrial process lines, it is desirable to be able to accurately predict when a particular valve or other piece of equipment will require repair, up to and including replacement, before the process line is shut down and opened up.

SUMMARY

In a system and apparatus according to some aspects, an acoustic emission sensor is arranged to detect the presence of cavitation inside and/or proximate a flow control device, such as a control valve, by sensing acoustic signals. The acoustic emission sensor is an electronic sensor arranged to sense acoustic energy traveling through a solid material. In some arrangements, the electronic sensor includes a piezoceramic or other piezoelectric acoustic emission sensor, a capacitive acoustic emission sensor, a laser interferometer acoustic emission sensor, and/or other equivalent types of electronic acoustic emission sensor. Preferably, the acoustic emission sensor is disposed on an outer surface of the flow control device. A processor is operatively coupled to the acoustic emission sensor. The processor is configured to receive acoustic information from the sensor and process the acoustic information to identify and/or monitor cavitation in the flow control device.

According to some aspects, methods of detecting and/or monitoring cavitation inside the flow control device include acquiring transient acoustic energy data with the acoustic emission sensor, filtering the data to select acoustic information corresponding to cavitation events, and determining cavitation levels based at least partly on one or more of the rate of cavitation events and the intensity of individual cavitation events.

According to some aspects, cavitation may be tracked over time. The cavitation levels may be used to determine an accumulation of cavitation within the flow control device over time. The accumulation may be useful for determining when maintenance should be performed on the flow control device. The processor may calculate a damage rate based on the accumulation of cavitation over time. The damage rate may be used to identify and/or to predict when the flow control device will need maintenance to repair components that are damaged by the accumulated occurrence of cavitation over time.

According to some aspects, the cavitation levels may be tracked and trended to determine whether the cavitation levels are increasing significantly. Trend information may be used to identify and/or to predict when the valve will need maintenance to repair valve components that are damaged by the cavitation. Trend information may be used to provide alerts to an operator, for example, to suggest changing operating conditions of a control valve.

According to some aspects, information relative to the position of a flow control member in the control valve may be used to identify potentially problematic operating conditions. Position information may be obtained, for example, from a positioner. The position information may be correlated with expected cavitation levels under normal flow conditions for one or more given positions. The expected cavitation level may be compared to an actual cavitation level. A significant deviation of the actual cavitation level with the expected cavitation level may indicate that a problem exists. An alert may be generated to indicate that further diagnostics may be appropriate.

In one exemplary arrangement according to the teachings of the present disclosure, an apparatus for sensing cavitation in fluid flowing through a flow control device includes an acoustic emission sensor and a processor. The acoustic emission sensor is configured to be disposed along a controlled fluid flow path extending through a body of the flow control device at a selected location, such as at or near a location likely to experience cavitation. The acoustic emission sensor is arranged to detect acoustic signals produced by cavitation within the fluid flow path. It is preferable to identify and capture the acoustic signals as individual and discrete occurrences of a transient elastic wave. The acoustic emission sensor is arranged to provide acoustic information based on the detected acoustic signals in the fluid flow path to the processor, such as by signals representative of the intensity of acoustic signals. The processor is operatively coupled with the acoustic emission sensor to receive the acoustic information. The processor is arranged to process the acoustic information and monitor cavitation levels in the fluid flow path based at least in part on a rate of cavitation events and an intensity of individual cavitation events extracted from the acoustic information.

In another exemplary arrangement in accordance with the teachings of the present disclosure, a method of monitoring cavitation levels in a flow control device for process liquids is disclosed. An acoustic emission sensor is coupled to an exterior wall of the flow control device and a processor is operatively coupled to the acoustic emission sensor to receive acoustic emission signals representative of transient acoustic energy data sensed in the fluid flow path by the acoustic emission sensor. The method includes acquiring at least one signal from the acoustic emission sensor with the processor; determining if the acquired signal corresponds to a cavitation event having predefined characteristics; recording selected characteristics of the acquired signal with the processor only if the acquired signals are produced by a cavitation event; and determining the cavitation level based on a rate of cavitation events and an intensity of each cavitation event.

In another exemplary arrangement in accordance with the teachings of the present disclosure, a method of monitoring an estimate of damage to a flow control device for process liquids caused by cavitation is disclosed. The method includes acquiring signals from the acoustic emission sensor with the digital signal processor. The acquired signals are associated with transient acoustic emission data within a pre-defined range of frequencies. Selected characteristics of the acquired signals are recorded with the digital signal processor only if the acquired signals are produced by a cavitation event wherein the acoustic signals and/or the acquired signals are within a predefined frequency range. Preferably, one or more filters are configured to filter the acoustic signals and/or the acquired signals to attenuate predefined unwanted frequencies above and/or below preselected respective upper and lower frequency limits. This filtering can occur one or more levels including within the acoustic emission sensor itself, within filtering hardware operatively disposed between the acoustic emission sensor and the digital signal processor, and/or with filtering software routines. A hit rate comprising the number of cavitation events that occur within a period of time is calculated. An intensity of each cavitation event is calculated, wherein the intensity is based on an energy unit per cavitation event. A cavitation level is determined based on the hit rate and the intensity. The number of times the cavitation level exceeds a predetermined threshold is tracked, whereby an estimate of accumulated damage to the flow control device caused by cavitation may be monitored.

In a further exemplary arrangement in accordance with the teachings of the present disclosure, a method of monitoring whether cavitation levels in a flow control device for process liquids are increasing includes calculating a trend of the hit rates and intensities with respect to time, and generating an alert that cavitation levels are increasing if the trend indicates that the hit rates and intensities are increasing over time.

According to some aspects and forms, the arrangement and interconnection of physical components of the system provides specific advantages in isolation from any computer programming and method aspects of the system. Similarly, in other aspects and forms, computer programming and/or methods embodying various aspects of processes disclosed herein provide specific advantages in isolation from some or all of the specific physical components of the system.

Other viable aspects and optional forms of the system, apparatus, and methods disclosed herein consistent with any one or more of the dependent claims and the following description will be apparent upon consideration of the following detailed description and the appended drawings.

BRIEF DESCRIPTION OF THE DRAWINGS

FIG. 2 is a logic flow diagram of a method of monitoring cavitation in a flow control device that may be implemented using the system of FIG. 1;

FIG. 3 is a detailed logic flow diagram of a step in FIG. 2;

DETAILED DESCRIPTION

Figure 1:
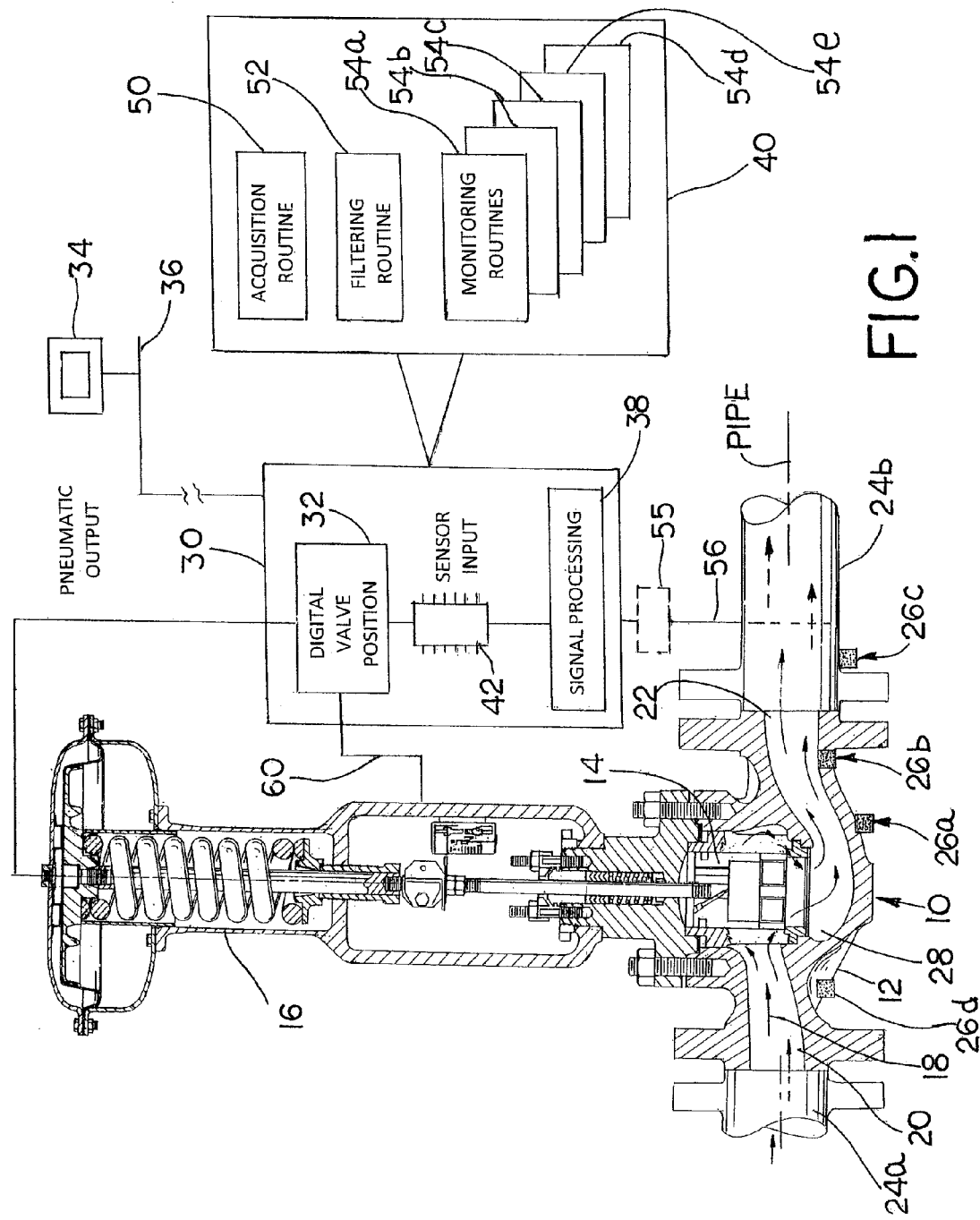
FIG. 1 is a partial cross-sectional view of a control valve in a process control line including a diagrammatic illustration of a system for sensing cavitation in fluid flowing through the control valve.

Turning now to the drawings, FIG. 1 illustrates a system 8 and apparatus for sensing and/or monitoring cavitation in liquid flowing through a control valve 10 or other flow control device according to the teachings of the present disclosure. The system 8 includes a flow control device, such as control valve 10 and/or pipes 24a and 24b, one or more acoustic emission sensors, such as acoustic emission sensors 26a-d, and a computerized processor, such as processor 30. The system 8 may be part of a larger process control plant, such as an oil refinery or chemical processing plant, as is understood in the art. For example, the system 8 may be integrated into a computerized control system for a process control plant, such as the system described in detail in U.S. Pat. No. 6,954,713, which is incorporated herein by reference in its entirety. The system 8 senses acoustic signals in fluid flow, such as acoustic signals generated by cavitation in or near the control valve 10, and identifies a cavitation flow condition based on the acoustic signals. The acoustic signals may include transient acoustic energy data caused by the formation of gas bubbles and/or the subsequent collapsing of the gas bubbles as part of the cavitation. The cavitation flow condition may be identified by the presence of cavitation events, which have preselected characteristics. Preferably, the system 8 monitors a cavitation level based on a rate of cavitation events and/or an intensity of individual cavitation events. The system 8 can provide a report of the cavitation flow condition in the liquid. The report may be provided to an operator and/or to a controller for the control valve 10. In some arrangements, the system 8 tracks accumulation of cavitation over time, which may be used to predict when maintenance should be scheduled on the control valve 10. In some arrangements, the system 8 monitors changes in the cavitation level, which may be used to provide an alert for statistically significant changes in the cavitation level. In some arrangements, the cavitation level may be correlated with a position of the control valve to identify potentially problematic operating conditions. Although the example shown in the drawings relates specifically to a control valve 10, the system 8 and apparatus and methods may be arranged to monitor cavitation in other types of flow control devices for process liquids, such as pipes and reducers, in a similar manner as described with respect to the example control valve 10.

The control valve 10 includes a valve body 12, a flow control member 14, and an actuator 16. A fluid flow path 18 extends through the valve body 12. The fluid flow path 18 extends at least partly from an inlet 20 into the valve body 12, through a throat 28, to an outlet 22 out of the valve body 12. The fluid flow path 18 may also be defined at least partly by a pipe 24a connected to the inlet 20 and/or a pipe 24b connected to the outlet 22. Additional components of the control valve 10 are well known and are not explained in further detail herein for the sake of brevity.

One or more of the acoustic emission sensors 26a, 26b, 26c, and 26d are disposed along the fluid flow path 18. Cavitation events that act on or near the inside surface of the valve body 12 are transmitted through the valve body to one or more of the acoustic emission sensors 26a-d. The acoustic emission sensors 26a-d detect acoustic signals and provide acoustic information representative of the detected acoustic signals. The acoustic signals sensed by the acoustic emission sensors may include, for example, vibrations and noise caused by the collapsing of bubbles within the fluid during cavitation. The acoustic signals also may include energy released in the valve body 12 when a bubble collapses close enough to the inner wall of the valve body that a small amount of damage occurs to the valve body. Preferably, the acoustic emission sensors 26a-d identify and capture the acoustic signals as individual and discrete occurrences of a transient elastic energy wave. As understood in the art, an elastic energy wave is an acoustic energy wave that is traveling through a solid, as opposed to an acoustic energy wave that is traveling through air or liquid. The acoustic information transmitted by the acoustic emission sensors 26a-d is preferably provided in the form of signals, such as electronic acoustic emission signals, generated in response to the sensed acoustic signals. The acoustic emission sensors 26a-d are preferably piezoelectric sensors, such as piezoceramic sensors, and may be high frequency piezoceramic sensors, such as the VS900-RIC acoustic emission sensors available from Vallen Systeme GmbH, of Icking, Germany, although other high frequency acoustic emission sensors may be used. In some arrangements, one or more of the acoustic emission sensors also or alternatively may include capacitive acoustic emission sensors, laser interferometer acoustic emission sensors, and/or other types of electronic acoustic emission sensors capable of detecting and receiving the acoustic signals produced by cavitation within or near the control valve 10.

The system 8 does not necessarily include each or all of the acoustic emission sensors 26a-d in all arrangements; however, preferably at least one of the acoustic emission sensors 26a-d is arranged to acquire the acoustic signals caused by cavitation. In the exemplary arrangement of FIG. 1, each of the acoustic emission sensors 26a-d is disposed at one or more selected locations, which may be selected based on the likelihood of experiencing cavitation caused by the control valve 10. The acoustic emission sensors 26a-d are arranged to detect acoustic signals emanating from fluid flowing along the fluid flow path 18 and passing as elastic waves through one or more solid components of the control valve 10, such as the wall of the valve body 12.

The acoustic emission sensors 26a-c are disposed on the valve body 12 and the pipe 24b at one or more locations where cavitation is most likely to occur. One common region where cavitation can occur is in the area of the fluid flow path 18 immediately downstream of the flow control member 14 and/or the trim, such as between the throat 28 and the outlet 22. Therefore, the acoustic emission sensors 26a and 26b are located at different selected locations along the fluid flow path 18 between the throat 28 and the outlet 22. For example, the acoustic emission sensor 26a is disposed adjacent the throat 28, and the acoustic emission sensor 26b is disposed adjacent the outlet 22. During cavitation, the formation of the gas bubbles can create a first acoustic signal pattern and the implosion of the gas bubbles can create a second acoustic signal pattern. The acoustic emission sensors 26a-c detect these first and second acoustic signal patterns and create electrical acoustic emission signals representative of these acoustic signal patterns in a manner well understood in the art. In this arrangement, the acoustic emission sensor 26a may be more likely to detect the formation of bubbles, or "flashing," and the acoustic emission sensor 26b may be more likely to detect the implosion of the bubbles. Cavitation may also occur or continue to occur further downstream of the outlet 22, such as in a region of the pipe 24b immediately adjacent the outlet 22. Therefore, the acoustic emission sensor 26c is disposed on the pipe 24b adjacent the connection with the outlet 22. The acoustic emission sensor 26c may also detect the implosion of the bubbles or may detect fewer bubble implosions or normal flow, i.e., flow without cavitation present.

The acoustic emission sensor 26d is disposed along the fluid flow path 18 at one or more locations proximate the control valve 10 that are not likely to experience cavitation. The acoustic emission sensor 26d may be located on an upstream side of the flow control member 14. For example, the acoustic emission sensor 26d may be coupled on an exterior surface the valve body 12 between the inlet 20 and the flow control member 14, as illustrated in FIG. 1, or on the pipe 24a. Because the acoustic emission sensor 26d is located where cavitation is not likely to occur, the acoustic emission sensor 26d provides baseline acoustic information that may be used as a baseline measure of normal flow, i.e., flow without cavitation present. The baseline acoustic information generated by the acoustic emission sensor 26d may be in the form of electrical acoustic emission signals called baseline emission signals. The baseline acoustic information may be compared against the acoustic information derived from the acoustic emission signals generated by the acoustic emission sensors 26a-c to calibrate the acoustic emission sensors 26a-c, detect the presence of cavitation in the fluid, and/or measure the intensity of cavitation.

Preferably, the acoustic emission sensors 26a-d are secured to the exterior of the respective valve body 12 and pipes 24a and 24b, i.e., on the side of the wall opposite the fluid flow path 18. In this arrangement, the acoustic emission sensors 26a-d can detect the acoustic signals from cavitation along the flow path 18 without breaching the boundary of the flow path. That is, the flow path 18 remains sealed without the acoustic emission sensors 26a-d or lead wires extending through the boundary wall, such as at a seal or flange. By not breaching the boundary of the flow path, the system 8 can acquire the acoustic signals in a manner that is less likely to cause leaks. The acoustic emission sensors 26a-d may be operatively coupled to the valve body 12 and/or the pipes 24a, 24b by any method sufficient to maintain the acoustic emission sensors 26a-d disposed on the respective valve body 12 and/or pipes 24a, 24b and able to adequately sense acoustic signals in the form of vibrations emanating from the liquid flowing along the fluid flow path 18. A preferred acoustic coupling for acoustic emission monitoring of cavitation is similar to the process described in ASTM standard E650 as is understood in the art. For example, it is typically important to maintain maximum face-to-face contact between the active detection area on the face of the acoustic emission sensor and the surface of the flow control device with a minimum of gaps or air space therebetween. Therefore, the acoustic emission sensors 26*a-d* may be coupled directly to the exterior surface of the respective valve body 12 and/or pipes 24*a*, 24*b*, for example with welds, fasteners, clamps, or adhesives. Preferably, the shape of the face of the acoustic emission sensor is complementary to the corresponding shape of the receiving surface of valve body or pipe. In some cases, a thin layer of grease or gel may be disposed between the receiving surface and the face of the sensor and manipulated so as to eliminate any air bubbles therebetween.

A thermal standoff (not shown) may be disposed between the face of the acoustic emission sensor and the receiving surface to insulate the acoustic emission sensor from the valve body. Use of a thermal standoff can be advantageous where the valve operates at high temperature or if access to the valve is limited. The thermal standoff may be a piece of metal with one or more exposed outside surfaces arranged to dissipate heat. Inclusion of a thermal standoff may also require some compensation and/or corrections to the acoustic emission signals to accommodate for variances caused by the thermal standoff.

The processor 30 is operatively connected to one or more of the acoustic emission sensors 26*a-d* to receive the respective acoustic information generated thereby. The acoustic information may be communicated in any suitable manner, such as by receiving the acoustic emission signals directly by a wired or wireless communication pathway or by indirectly receiving the acoustic information via other possible communication pathways. Preferably, the acoustic information is provided in the form of electric acoustic emission signals generated by the acoustic emission sensors 26*a-d* in response to the sensed acoustic signals. The processor 30 is configured to identify and monitor the presence of cavitation in the fluid flow path 18 based on the acoustic information received from any one or more of the acoustic emission sensors 26*a*, 26*b*, 26*c*, and/or 26*d*. The processor 30 is also configured to extract data from the acoustic information and use the acoustic information to determine additional information about or relevant to the control valve 10 based on the monitored cavitation. The processor 30 may be dedicated to monitoring the presence of cavitation at the flow control device, or the processor 30 may be integrated with other computerized systems that perform other process control functions. For example, the processor 30 may be integrated with a positioner 32 for controlling the position of the flow control member 14. The positioner 32 may be a typical digital valve positioner, such as a Fisher Fieldview™ DVC6000 digital valve controller, available from Emerson Process Management, of Mashalltown, Iowa. The processor 30 may be connected to and/or integrated with one or more other plant control system computers 34, for example, with a bus 36.

In one arrangement, the processor 30 includes a digital signal processor (DSP) 38, one or more digital or other electronic memory modules 40, one or more computer processors 42, and other known computer components, such as input/output devices, data communication devices, application specific integrated circuits (ASICs), and/or software modules for accomplishing the functions and methods described herein in a manner that would be understood by a person of ordinary skill in the digital signal processing and computing arts. The DSP 38 may include an analog-to-digital (AD) converter. In other arrangements, the processor 30 may include embedded signal processing routines to process the acoustic emission signals received from the acoustic emission sensors 26*a-d* instead of a dedicated DSP 38. The computer processor 30 may include all of the functional components above in a single unit or one or more of the components may be remote and operatively connected by any known data communication arrangement, such as via the Foundation™ Fieldbus protocol, HART protocol, internet, Ethernet, and/or or other suitable data communication arrangements as would be understood by a person of ordinary skill. Data communication between various components of the system 8 may be via one or more wired connections and/or wireless connections.

The processor 30 includes program instructions or is arranged to access such program instructions implemented by means of appropriate hardware and/or software sufficient to receive the acoustic information generated by the acoustic emission sensors 26*a-d* and to process the received acoustic information in a method sufficient to monitor cavitation levels in the fluid flow path based on the rate and intensity of individual cavitation events. To accomplish this, one or more routines, preferably in the form of sets of programming instructions, are accessible to the processor 30. In one arrangement, an acquisition routine 50, a filtering routine 52, and one or more monitoring routines 54*a*, 54*b*, 54*c*, and 54*d* are stored in the memory 40. In other arrangements, the programming instructions may also or alternatively be embedded directly within the computer processor 42 and/or may be stored elsewhere and accessed remotely by the computer processor 42. The acquisition routine 50 causes the processor 30 to receive the acoustic information generated by the acoustic emission sensors 26*a-d*, such as by receiving the acoustic emission signals ("AE signals"). The filtering routine 52 filters the received AE signals to select only signals that meet one or more predefined characteristics indicative of cavitation at the control valve 10 and ignoring other signals. In some arrangements, filtering may also or alternatively be performed by filtering of the acoustic signals by the acoustic emission sensors 26*a-d* and/or by filtering hardware 55. The filter hardware 55 is operatively located between the acoustic emission sensors 26*a-d* and the processor 30 so as to filter the acoustic emission signals prior to being received at the processor 30. The monitoring routines 54*a-d* use the selected signals to identify and monitor cavitation in the control valve 10 according to various criteria. Together, the acquisition routine 50, filtering routine 52, and one or more of the monitoring routines 54*a-d* may be configured to implement one or more of the methods described in detail hereinafter. The routines 50, 52, and 52*a-d* may be instructions in the form of software, for example stored in the memory 40, and/or hardware, such as dedicated circuits within the computer processor 42, the DSP 38, the positioner 32, and/or the sensors 26*a-d*.

With reference to FIGS. 2 and 3, a method 100 of monitoring cavitation in a flow control device, such as the control valve 10 and/or the pipes 24*a* or 24*b*, is illustrated. The method is implemented by the system 8 of FIG. 1. The system 8 is configured to acquire acoustic signals from fluid flowing through the flow control device with any one or more of the acoustic emission sensors 26*a-d* within a range of frequencies preselected for being likely to be indicative of cavitation. The acquired acoustic signals preferably include transient acoustic energy data generated by cavitation. The system 8 may be configured to provide a level of filtering at the acoustic emission sensors, for example, by adjusting sensitivity parameters of the acoustic emission sensors, selecting acoustic emissions sensors with predefined sensitivity ranges, and/or adjusting output parameters for the acoustic emission signal output by the acoustic emission sensors. In some arrangements, the acoustic emission sensors 26a-d are configured to filter the acoustic signals so as to provide a first level of filtering by only acquiring acoustic signals within the range. For example, the range in some arrangements is between approximately 500 kHz and approximately 1600 kHz, but other ranges may be used. The system 8 may be configured to provide a level of filtering between the acoustic emission sensors and the processor 30, for example, with filtering hardware 55 operatively located between the acoustic emission sensors and the processor 30. The system may be configured to provide a level of filtering, for example, by adjusting receiving limit parameters at the processor 30, such as with instruction routines or programs implemented from software or hardware. The receiving limit parameters may include one or more parameters within the AD converter, DSP 38, or other hardware or software components of the processor 30. The processor 30 receives acoustic information in the form of AE signals from one or more of the acoustic information sensors 26a-d about acoustic signals caused by transient events that occur with each bubble formation, cavity, or bubble collapse during a cavitation event within the flow control device and uses the data to calculate a cavitation level.

Block 102 acquires acoustic signals from the flow control device at least within the preselected range of frequencies. In one arrangement, the acoustic signals are acquired initially by one or more of the acoustic emission sensors 26a-d. The acoustic emission sensors 26a-d are configured to acquire transient acoustic energy data within a range of frequencies, such as at least between approximately 500 kHz and approximately 1600 kHz. Acoustic signals acquired by either of the sensors 26a and 26b, for example, may be used to provide direct acoustic information regarding cavitation occurrences within the flow control valve 10 downstream of the throat 28. Acoustic signals acquired by the sensor 26c may provide direct information regarding cavitation occurrences within the pipe 24b adjacent the downstream outlet 22 of the control valve 10. Acoustic signals acquired by the sensor 26d may provide control or baseline information relative to standard liquid flow without cavitation. For purposes of the following descriptions, the acoustic signals are obtained by the acoustic emission sensor 26a; however, the same process may be followed for any one of the acoustic emission sensors 26a-d. The acoustic emission sensor 26a then generates acoustic information in the form of an AE signal representative of the acquired transient acoustic energy data. The AE signal is communicated to the processor 30, for example, via wires 56 and/or other suitable electronic data communication pathway. The block 102 may be executed, for example, by the acquisition routine 50 of the processor 30.

Block 104 determines if the AE signal from block 102 is caused by a cavitation event according to predefined parameters. A cavitation event is defined by one or more predefined characteristics of the AE signal. In one arrangement, a cavitation event is defined as an acquired AE signal that is above a predefined minimum threshold and within a predefined filter range. The filter range can include the minimum threshold (i.e., a low end) and a predefined maximum cutoff (i.e., a high end). For example, an entire AE signal waveform may be considered based on amplitude and frequency of the signal. The amplitude of the AE signal waveform is representative of the acoustic energy decibels ($dB_{AE}$) of a given waveform. Preferably, the $dB_{AE}$ is measured in microvolts and reported in $dB_{AE}$ by calculating −20 Log 10 (Peak Amplitude Voltage/1 microvolt). It may be determined whether the waveform of the AE signal meets one or more threshold parameters, such as an amplitude within a specified range and/or the hit rate of high amplitude waveforms. However, other threshold and filter parameters may be used. If the AE signal exceeds the predetermined minimum threshold and is within the predefined filter range, then the AE signal is considered to be a "hit" caused by a cavitation event that, for example, may affect the maintenance of the flow control device. In this case, the AE signal is selected as being caused by a cavitation event and control transfers to block 106. If the AE signal does not exceed the predetermined minimum threshold and is not within the predefined filter range, then the AE signal is ignored and control returns to block 102 to acquire another AE signal from the acoustic emission sensor 26a. The block 104 may be executed, for example, by the filtering routine 52 of the processor 30.

Figure 2A:
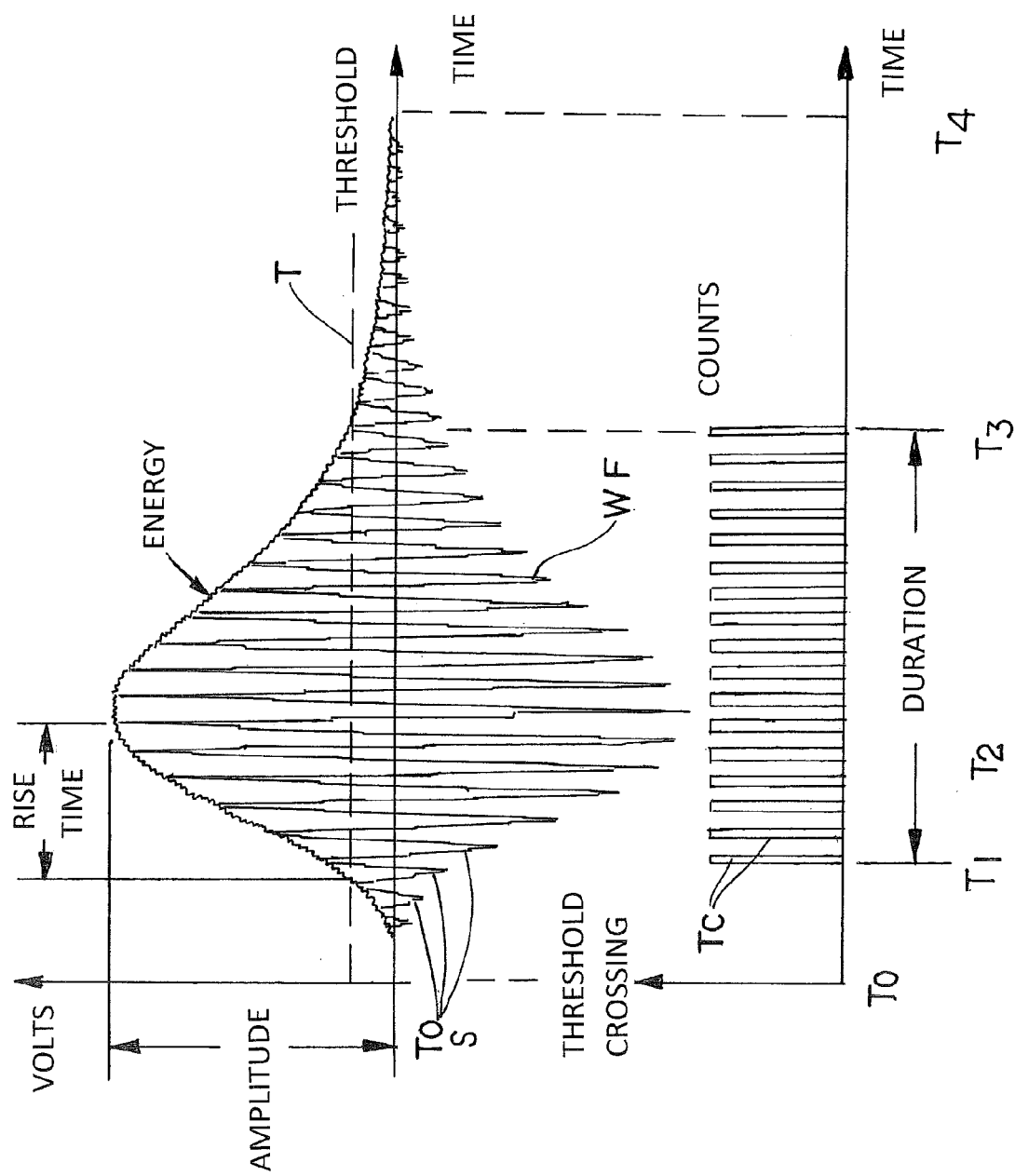
FIG. 2A is a pair of correlated graphs charting the amplitude and threshold crossings for a series of acoustic emission signals during an idealized period of cavitation flow.

Block 106 records preselected characteristics of the selected AE signal from block 104 representative of various acoustic information from the cavitation event captured by the acoustic emission sensor 26a. With reference to FIG. 2A, individual cavitation events typically occur in groups during a period of cavitation flow. FIG. 2A illustrates an example waveform WF for a transient event that may be similar to a group of cavitation events during a period of cavitation flow. The upper graph shows the voltage of acquired signals S and the lower graph shows threshold crossings of the signals. The sensor output voltage, as illustrated in the upper graph, is typically reported in acoustic energy decibels (i.e., $dB_{AE}$). The signals S start at time t0 with no cavitation events, cross a predetermined threshold level T at time t1, rise to a peak amplitude at time t2, fall back below the threshold level T at time t3, and fall to no cavitation events at time t4. Other characteristics may include additional individual features of the acquired signal S, such as the number, rate, and/or time duration of threshold crossings TC within the group, rise time from a first threshold crossing to a largest amplitude acquired signal S within the group of hits, and accumulated energy of a group of hits, each of which are well understood in the art of acoustic waveform processing. The threshold crossings TC may correspond to the hits and counts discussed in detail hereinafter relative to FIG. 4.

Returning to FIG. 2, block 108 determines a cavitation level value from the characteristics recorded at block 106. The cavitation level is determined based on the rate of cavitation events and the intensity of the cavitation events. In one exemplary method, illustrated in FIG. 3, block 108 includes a first calculation related to the rate of cavitation events at block 110, a second calculation related to the intensity of each cavitation event at block 112, and a third calculation related to the cavitation level value at block 114.

Block 110 calculates a hit rate by recording the number of cavitation events that occur during a selected period of time. For example, the hit rate H may be the number of cavitation events N that occur during a period of time t immediately preceding the present time T divided by the period of time. This may be represented as the equation: $H = N_{T-t}/(T-t)$. In most situations, the hit rate is calculated as the number of cavitation events that occur over a period of time of at most up to a few seconds, such as between about 1 second and about 10 seconds. However, longer or shorter periods of time may be used in some situations. The hit rate is reported as the number of cavitation events per second during that period of time. With reference to FIG. 2A, in one example, a hit rate R may be calculated as the number of individual threshold crossings TC that occur during of a given period of cavitation flow (e.g., from t1 to t3) divided by the duration of the period of cavitation flow (e.g., t3−t1).

Block 112 calculates an intensity of each individual cavitation event based on the characteristics recorded at block 106. The intensity is based on a measure of energy released by the cavitation event. For example, the intensity may be correlated with the amplitude, duration, area under the wave, and/or other individual features of the acquired signal S. In one arrangement, the intensity is determined as the absolute value of the area under one waveform or a group of waveforms, as illustrated in FIG. 2A. Energy may be calculated as the integration of the sensor output voltage squared over time, i.e., Energy=Integral($v^2$)(dt), where v is the sensor output voltage and dt is the change in time, as is understood in the art. Blocks 110 and 112 may be performed in any order or simultaneously.

Block 114 calculates a value of the cavitation level based on the hit rate calculated at block 110 and the intensity calculated at block 112. The value of the cavitation level is preferably calculated as a function of both the hit rate and the intensity. That is, C=f(R,i), where C is the cavitation level, R is the hit rate, I is the intensity. Preferably, the cavitation level is directly proportional to the hit rate and the intensity. Different specific equation relationships can be used to calculate the cavitation level C depending on the specific data received and the specific form of the output desired.

The blocks 106-114 may be executed, for example, by the monitoring routine 54a of the processor 30.

The cavitation level determined by the method 100 may have several different uses, such as determining if cavitation is occurring, determining an intensity of cavitation activity at some point in time, and/or tracking an accumulation of cavitation and/or damage over a period of time. This information may be useful, for example, in monitoring performance of the flow control device, identifying non-ideal functioning of the flow control device, and/or predicting maintenance needs without disassembling or having total failure of the flow control device. The following methods build on the method 100 to utilize the information regarding cavitation levels provided by the method of monitoring.

Figure 4:
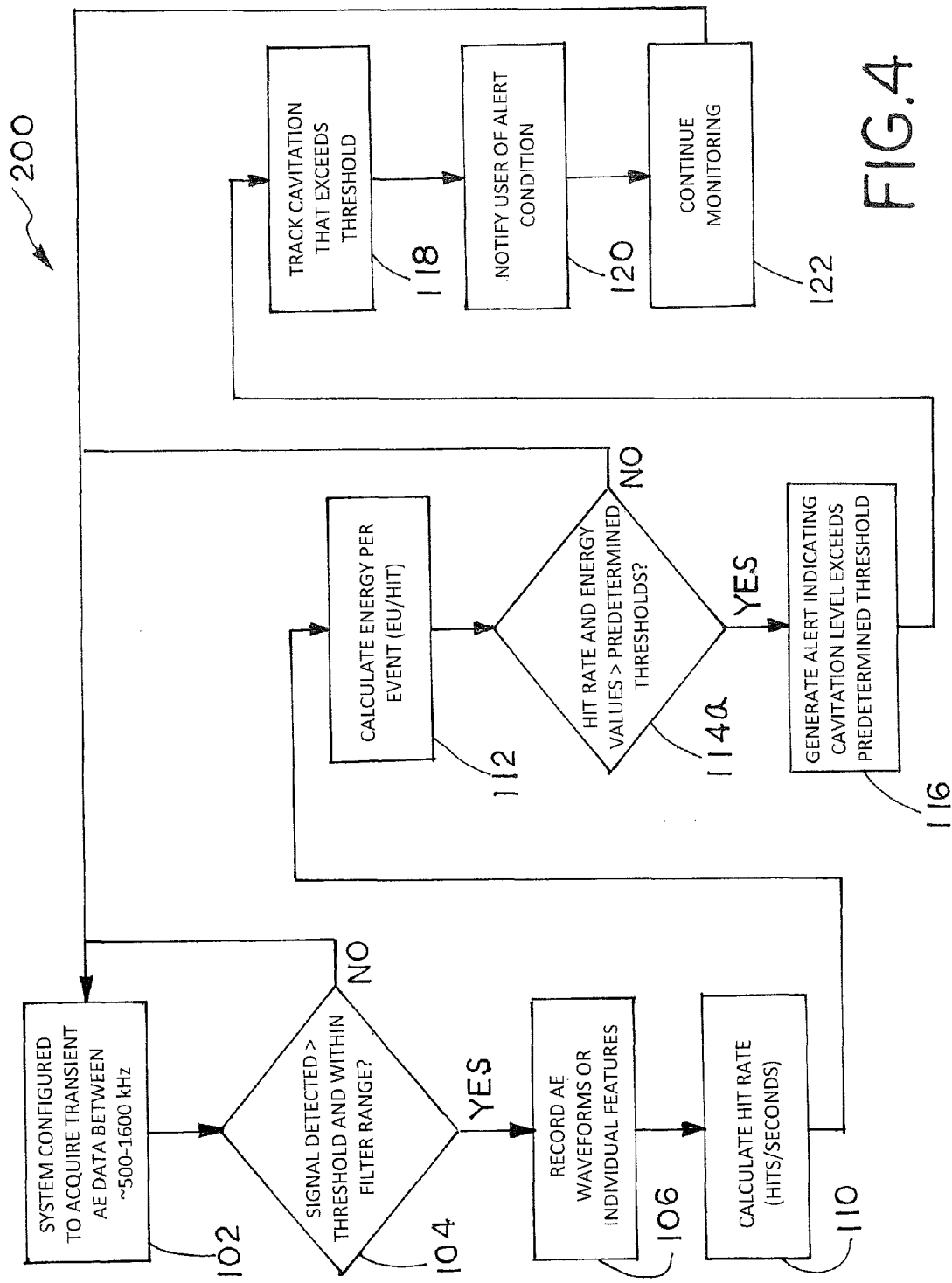
FIG. 4 is a logic flow diagram of another method of monitoring cavitation in a flow control device that may be implemented using the system of FIG. 1.

FIG. 4 illustrates another method 200 of monitoring cavitation of that may be useful, for example, for estimating damage to a flow control device, such as the control valve 10. The method 200 may be implemented with the system 8 illustrated in FIG. 1. The method 200 includes steps of the method 100 for monitoring cavitation levels and uses the information about the cavitation levels to monitor the cavitation over a period of time, and to monitor an accumulation of cavitation activity over time. The information may be used to estimate the amount of damage sustained by the flow control device, to track the damage, and/or to predict and/or plan for maintenance to repair the damage.

The system of FIG. 1 is configured to acquire transient acoustic energy data from any one or more of the acoustic emission sensors 26a-d within a selected frequency range, as described in detail previously in relation to the method 100.

At block 102, the system of FIG. 1 acquires transient acoustic energy data from any one or more of the acoustic emission sensors 26a-d at least within a preselected range of frequencies and generates AE signals, as described in detail previously.

At block 104, the processor 30 determines whether the AE signal is caused by a cavitation event according to predefined parameters and selects a signal for further processing if it is within the predefined parameters, as described in detail previously.

At block 106, the processor 30 records selected characteristics of the selected signal, such as the waveform or other individual features of the acoustic emission signal, as described in detail previously.

At block 110, the processor 30 determines the rate of cavitation events, for example, by calculating the hit rate as described previously.

At block 112, the processor 30 determines the intensity of each cavitation event, for example by calculating the amount of energy per cavitation event as described previously.

At block 114a, the processor 30 calculates a cavitation level and determines whether the cavitation level exceeds a predetermined cavitation level threshold. If the cavitation level exceeds the predetermined cavitation level threshold, then control passes to block 116. If the cavitation level does not exceed the predetermined cavitation level threshold, then control returns to the block 102 to acquire another AE signal. In one exemplary arrangement, the determination of whether the cavitation level exceeds the predetermined cavitation level threshold may include an independent comparison of each or either of the hit rate and the intensity with separate threshold values for the cavitation event. The hit rate calculated at block 110 is compared with a predetermined hit rate threshold value. The intensity is compared with a predetermined intensity threshold value. In some arrangements, the cavitation level is determined to exceed the predetermined cavitation level threshold if both the hit rate and the intensity exceed the respective hit rate threshold value and the intensity threshold value. In other arrangements, the cavitation level is determined to exceed the predetermined cavitation level threshold if either the hit rate or the intensity exceed the respective hit rate threshold value and the intensity threshold value. In another exemplary arrangement, the cavitation level is calculated as described previously for the block 114 of FIG. 3 as a composite value depending on each of the hit rate and the intensity. The composite value of the cavitation level is compared with a predetermined composite cavitation level threshold value. If the composite value exceeds the composite cavitation level threshold, then the cavitation level is determined to exceed the predetermined cavitation level threshold. A further exemplary arrangement may include a combination of the previous two exemplary arrangements. Under any of these schemes, the cavitation level calculated is a function of both the rate of cavitation events and the intensity of the individual cavitation events, and is preferably a directly proportional function, as explained previously. If the cavitation level does not exceed the predetermined cavitation level threshold, then control returns to block 102 to acquire another AE signal from one or more of the acoustic energy sensors 26a-d. If the cavitation level exceeds the predetermined cavitation level threshold, then the processor 30 institutes further monitoring protocols that may, for example, be used to estimate damage to the flow control device, which may be performed in one or more steps of blocks 116, 118, and 120, described hereinafter.

Block 116 generates an alert indicating that the cavitation level exceeds the predetermined threshold value or values. The alert is preferably generated by the processor 30.

Block 118 tracks the number of times and/or the amount of time that the cavitation level exceeds a predetermined threshold so that an estimate of accumulated damage to the flow control device caused by cavitation may be monitored. In some arrangements, the block 118 increments a counter for the number of times the cavitation level has been determined to exceed the predetermined cavitation level. The block 118 may increment the counter each time an alert is generated at block 116, or the block 118 may increment the counter in direct response to the positive determination at block 114a without generating the alert at block 116. The counter is preferably a digital electronic counter within the processor 30, such as stored within an electronic memory, database, and/or other digital counter mechanism; however, other types of counters, such as an analog counter, may be used. In some arrangements, the block 118 tracks the accumulated amount of time that the cavitation level exceeds the predetermined threshold. The block 118 may identify the time duration of each incidence during which the cavitation level exceeds the predetermined threshold and additively accumulate each such time duration. The additive accumulation would represent the accumulated amount of time that the cavitation level exceeds the predetermined threshold.

Block 120 provides a notification to a user of the existence of an alert condition. The notification may be generated by the processor 30, for example, in the form of an electronic notification sent to a display screen.

Block 122 returns control to the block 102.

The count accumulated by the counter at block 118 may be used to estimate and/or track damage to the flow control device. Specifically, the count can be a proxy for the amount of damage sustained by the flow control device over time. The count may be correlated to estimations of damage of the flow control device by correlations between the number of cavitation events accumulated and the amount of damage sustained by the flow control device. For example, as the count (i.e., the number cavitation events above the predetermined cavitation level threshold) increases, the estimated accumulated damage to the flow control device is assumed to also increase. The correlation may be linear, non-linear, exponential, or another suitable relation that, for example, can be determined experimentally and/or theoretically. Thus, a large number of counts may indicate an estimate of a large amount of damage to the flow control device caused by cavitation. Conversely, a low number of counts may indicate an estimate of a low amount of damage to the flow control device caused by cavitation.

The count accumulated by the counter may be used to identify when the flow control device needs to be serviced to repair damage caused by or indicated by cavitation. For example, the count may be set to zero when the flow control device is new and undamaged. When the count reaches a predefined limit value, the flow control device may be designated for service. In some arrangements, a report may be created indicating that the control valve 10 is due for service when the count reaches some predetermined limit value. In this arrangement, the estimation of damage is based on an accumulation of damage that is dependent on one or both of the rate and intensity of cavitation events in the flow control device. Further, the estimation of damage may be adjusted to weight the estimate more or less on either of the rate or the intensity of the cavitation events. The predetermined limit value may be determined experimentally and/or theoretically.

The count in some arrangements may be used to predict a time in the future when the flow control device should be serviced to repair damage caused by or indicated by cavitation. For example, a velocity of the alerts, i.e., a rate of the number of alerts per some increment of time, may be used in conjunction with the accumulated sum of alerts over a period of time to predict a time in the future that the predetermined limit value will be reached.

Blocks 116, 118, 120, and 122 may be implemented sequentially or simultaneously. Further additional functional steps or fewer functional steps may be implemented in estimating and/or tracking damage caused to the flow control device by cavitation. Blocks 114a-122 may be executed, for example, by the monitoring routine 54b of the processor 30.

Figure 5:
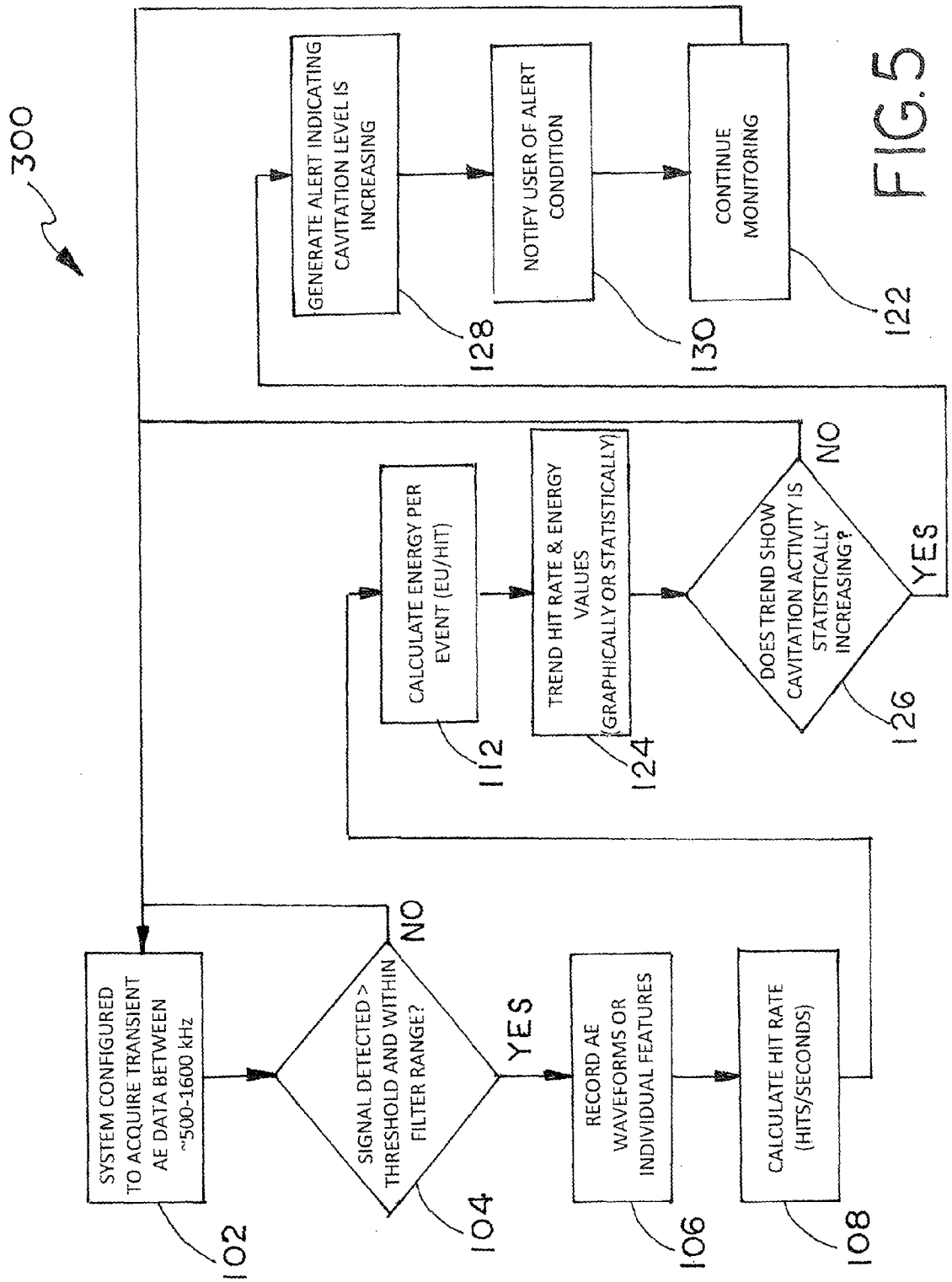
FIG. 5 is a logic flow diagram of a further method of monitoring cavitation in a flow control device that may be implemented using the system of FIG. 1.

FIG. 5 illustrates a method 300 of monitoring cavitation that may be used to monitor a damage rate to a flow control device, such as the control valve 10. The method 300 may be implemented with the apparatus illustrated in FIG. 1. The method 300 includes steps of the methods 100 and 200 for monitoring cavitation levels and uses the information about the cavitation levels to determine information that may be used to estimate the rate of damage sustained by the flow control device.

The system of FIG. 1 is configured to acquire transient acoustic energy data from any one or more of the acoustic emission sensors 26a-d between approximately 500 kHz and approximately 1600 kHz, preferably in the same manner as described previously relative to methods 100 and 200. In addition, blocks 102, 104, 106, 108 and 112 are implemented by the processor 30 in the same manner as previously described relative to methods 100 and 200, the description of which is not repeated here for brevity.

Block 124 calculates one or more trends of the cavitation events. In one arrangement, block 124 determines a trend of the hit rate and a trend of the intensity values. The trends may be determined graphically and/or statistically. For example, if the hit rate is increasing over a sample time period, a hit rate trend may be positive, if the hit rate is decreasing over the sample time period, the hit rate trend may be negative, and if the hit rate is remaining unchanged over the sample time period, the hit rate trend may be steady (i.e., zero). Similarly, if the intensity values are increasing, decreasing, or remaining unchanged over a sample time period, an intensity trend may be positive, negative, or steady, respectively. The sample time period may be selected to be any suitable time period. For example, the sample time period may be a period of seconds, minutes, hours, days, weeks, or longer or shorter, depending on the sensitivity desired. The sample time periods for each of the hit rate trend and the intensity trend may be the same or different from each other. In another arrangement, block 124 determines a trend that combines and incorporates each of the hit rate data and intensity data into a composite cavitation activity trend. The composite cavitation activity trend may be calculated with different weightings and/or additional information as desired.

Block 126 determines whether one or more of the trends calculated at block 124 shows whether cavitation activity within the flow control device is increasing in a statistically significant manner. Statistical significance may be determined in many ways. For example, statistical significance may be based on a rolling average and/or on a selected standard deviation multiple of a selected variable. For example, the block 126 may determine whether a rolling average of the trends calculated at block 124 exceeds a preselected value and/or if the cavitation activity is increasing at a rate that exceeds a preselected rate within a preselected level of statistical significance relative to a standard deviation. If so, then control passes to block 128. Otherwise, control returns to the block 102.

Block 128 generates an alert that indicates that the cavitation level is increasing. At block 130, the processor 30 notifies a user that the cavitation level is increasing. Blocks 128 and 130 may be executed in any desired order. The alert generated at block 128 may be used, for example, to monitor the flow control device for increases in normal levels of cavitation that may be indicative of some problem, such as a malfunction or maintenance need, that would not otherwise be readily visible to an operator from a visual inspection or other information.

At block 122, control returns to block 102 to continue monitoring for transient acoustic energy data from the flow control device.

The blocks 122-130 may be executed, for example, by the monitoring routine 54c of the processor 30.

In some arrangements, two or more of the methods 100, 200, and 300 may be implemented together or simultaneously to provide a several types of information to a user. For example, blocks 102 through 112 may be executed sequentially, and then two or more of each of block 114, blocks 114a through 120, and blocks 124 through 130 may be executed to provide each of a cavitation level, an estimate of accumulated damage, and a damage rate.

In some arrangements, one or more of the acoustic emission sensors 26a-d are integrated with the positioner 32. In some arrangements, one or more of the acoustic emission sensors 26a-d are integrated with asset management software of the computerized control system of a process control plant. In some arrangements, one or more of the acoustic emission sensors 26a-d are integrated with a process control system in a process control plant. For example, any one or more of the acoustic emission sensors 26a-d could be tied directly to its own dedicated processor 30, or may be implemented as a component of the positioner 32, the DSP 38, or higher level process software, including asset management software, such as the AMS Suite available from Emerson Process Management, or top level process control system, such as the DeltaV digital automation system from Emerson Process Management.

In some arrangements, the processor 30 is configured to identify a problematic flow condition based on the position of the control member 14. The processor 30 is configured to receive position information about the position of the flow control member 14 from the positioner 32. The position information is used to identify potentially problematic operating conditions based on the cavitation level determined by any one of methods 100, 200, or 300. The position information may be correlated with expected cavitation levels for different positions, and the expected cavitation level is compared with an actual cavitation level, such as calculated at bock 114. For example, it may be found experimentally that the amount of cavitation in a given control valve varies according to some identifiable function of the position of the flow control member 14 under some given flow conditions. A significant deviation in the actual cavitation level from the expected cavitation level may indicate that the flow control member 14 is not in the position it is supposed to be in, that a component is broken or significantly worn, or that the flow conditions are different than the given flow conditions. Thus, a significant deviation between the expected cavitation level and the actual cavitation level may serve as a proxy to identify potential problems with the control valve and/or the flow conditions through the control valve 10, which may require further investigation.

Figure 6:
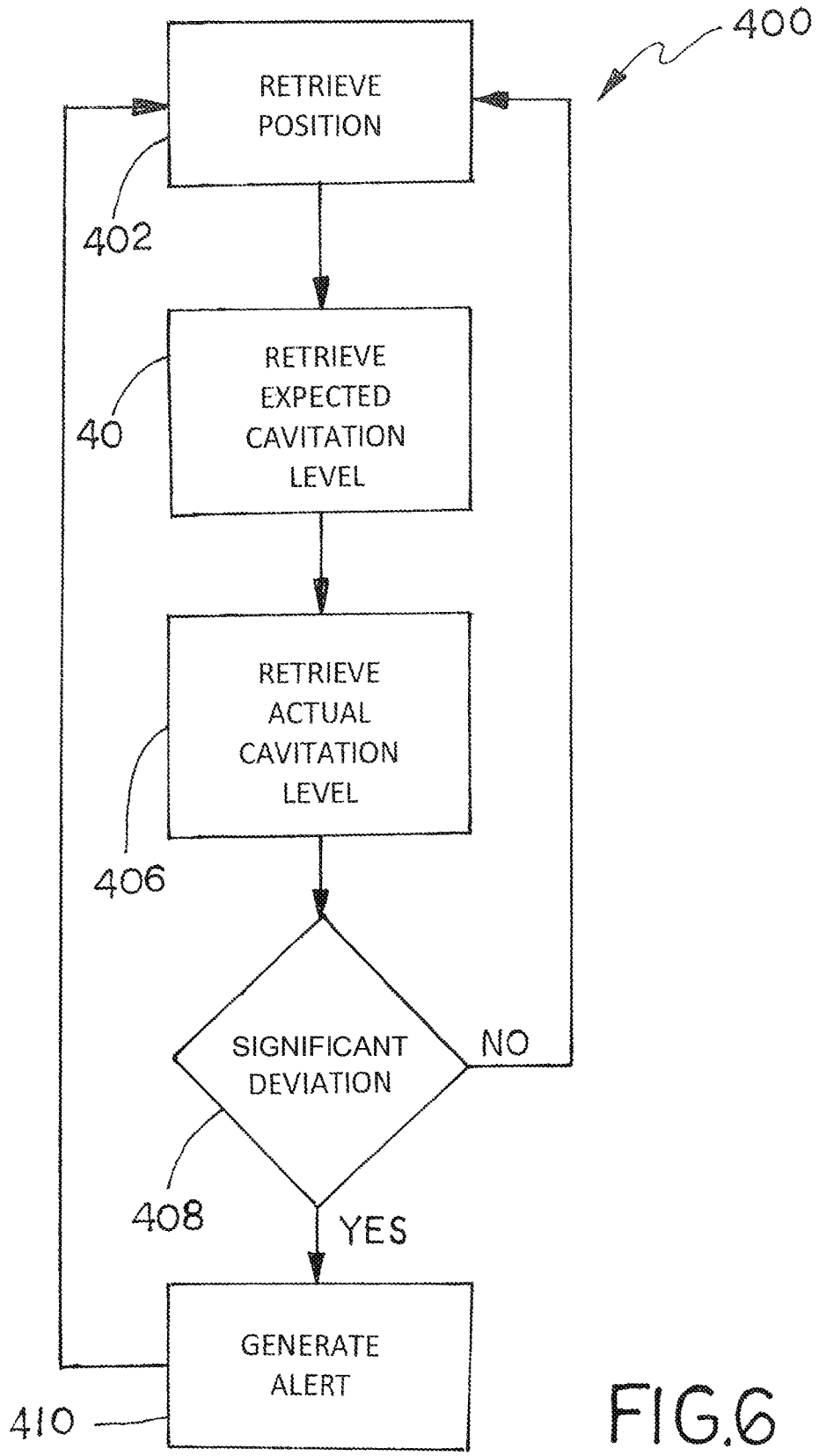
FIG. 6 is a logic flow diagram of a still further method of monitoring cavitation in a flow control device that may be implemented using the system of FIG. 1.

In one exemplary arrangement, the routine 54d is implemented by the processor 30 to execute a method 400, illustrated in FIG. 6. Block 402 retrieves position information from the positioner 32, for example via wires 60 or other suitable communication pathway. Block 404 retrieves an expected cavitation level correlated to that position. The expected cavitation level may be retrieved, for example, from a database in the memory 40. Block 406 retrieves the actual cavitation level, for example, from the block 114 or 114a. Block 408 compares the actual cavitation level with the expected cavitation level. If the actual cavitation deviates significantly from the expected cavitation, then an alert is generated at block 410. The alert may be provided to an operator or other components of the process control system to indicate that further diagnostics of the control valve 10 may be needed. Whether a deviation is considered significant is determined by a preselected level of significance, which may be selected according any desired set of parameters. The method 400 may return back to block 402 after either of blocks 408 or 410 as indicated. In some arrangements, the alert is provided to an operator to alert the operator to change the operating position of the valve.

In some arrangements, the processor 30 is configured to differentiate between a normal flow condition and a cavitation flow condition above a predefined threshold cavitation level, and generate a report relative to the differential. At least two ways of calculating the differential may include: 1) calculating a differential between two locations at the same time, called a "position differential," and 2) calculating a differential between two times (e.g., at t0 and T) at the same location, called a "temporal differential." To determine a position differential, for example, a baseline "normal" flow condition may be identified by using baseline acoustic signals from the acoustic emission sensor 26d to define a normal flow condition that does not have an elevated cavitation level. To determine a temporal differential, for example, a baseline "normal" flow condition may be identified when the flow control device is new and operating under conditions known or assumed to not have an elevated cavitation level. The processor 30 may include a routine 54e to compare the acoustic information associated with normal flow conditions with corresponding acoustic information from the acoustic information sensors 26a-c to determine a difference between the baseline or normal flow condition and the flow conditions in the areas likely to experience cavitation. The differences may be generated into one or more reports, which may be used for further analysis and guidance relative to operation and/or maintenance of the flow control device.

INDUSTRIAL APPLICABILITY

A system, apparatus, and/or method according the teachings of the present disclosure is useful for monitoring cavitation in liquid flowing through a process control device, such as a control valve or pipe, as described in the technical example provided herein. However, the system, apparatus, and/or method may have other uses and/or benefits, and the disclosure is not limited to the examples elucidated herein. The ability to sense the presence of cavitation within or proximate a control valve or other flow control device, in some arrangements, can be useful to allow adjustment of the process conditions through the control valve. It may also, in some arrangements, be useful for planning maintenance to repair damage to the control valve and/or adjacent piping components caused by cavitation.

The technical examples described and shown in detail herein are only exemplary of one or more aspects of the teachings of the present disclosure for the purpose of teaching a person of ordinary skill to make and use the invention or inventions recited in the appended claims. Additional aspects, arrangements, and forms within the scope of the appended claims are contemplated, the rights to which are expressly reserved.

What is claimed:

1. An apparatus for sensing cavitation in fluid flowing through a flow control device, the apparatus comprising:
an acoustic emission sensor configured to be disposed along a controlled fluid flow path extending through a body of the flow control device at a first selected location, wherein the acoustic emission sensor is arranged to detect acoustic signals produced by cavitation within the fluid flow path and to provide acoustic information based on the detected acoustic signals; and
a processor operatively coupled with the acoustic emission sensor and arranged to receive the acoustic information from the acoustic emission sensor, wherein the processor is arranged to process the acoustic information and monitor cavitation levels in the fluid flow path at least partly based on a rate of cavitation events and an intensity of individual cavitation events extracted from the acoustic information,
wherein the processor differentiates between different flow conditions in the fluid flow path, including between a normal flow condition and a cavitation flow condition above a predefined threshold cavitation level, and generates a report of the flow condition in the fluid flow path.

2. The apparatus of claim 1, wherein the flow control device comprises a control valve, wherein the body comprises a valve body of the control valve, and wherein the acoustic emission sensor is coupled to an exterior surface of the valve body and arranged to detect elastic waves produced by the cavitation and transmit signals arranged to provide the acoustic information to the processor.

3. The apparatus of claim 1, wherein the processor monitors an accumulation of cavitation levels over time.

4. The apparatus of claim 3, wherein the processor predicts a maintenance need based on the accumulation of cavitation levels.

5. The apparatus of claim 1, wherein the processor monitors a rate of estimated damage to the valve caused by the cavitation based on the cavitation levels.

6. The apparatus of claim 5, wherein the processor predicts a maintenance need based on the rate of estimated damage.

7. The apparatus of claim 1, wherein the flow control device is a pipe, and wherein the acoustic emission sensor is coupled to an exterior surface of the pipe and arranged to detect elastic waves produced by the cavitation and transmit signals to provide the acoustic information to the processor.

8. The apparatus of claim 1, wherein the processor differentiates between the different flow conditions based on at least one of frequency, amplitude, rise time, energy, and counts of signals provided by the acoustic emission sensors.

9. The apparatus of claim 1, further comprising:
a second acoustic emission sensor disposed along the fluid flow path at a second selected location, wherein the second acoustic emission sensor provides baseline acoustic information representative of acoustic signals sensed in the fluid flow path under the normal flow conditions.

10. The apparatus of claim 1, further comprising:
a digital valve positioner operatively coupled with the processor and with the control valve, the positioner arranged to control a position of a flow control member of the control valve, wherein the digital valve positioner receives position data representative of a position of the flow control member, and wherein the digital valve positioner correlates the acoustic information with the position and thereby identifies non-ideal flow conditions in the fluid flow path.

11. The apparatus of claim 1, wherein the acoustic emission sensor is integrated with at least one of a digital valve positioner, asset management software, and a process control system, within a computerized control system for a process control plant.

12. A method of monitoring cavitation levels in a flow control device for process liquids, wherein an acoustic emission sensor is coupled to an exterior wall of the flow control device and a processor is operatively coupled to the acoustic emission sensor to receive acoustic emission signals representative of transient acoustic energy data sensed in the fluid flow path by the acoustic emission sensor, the method comprising:
acquiring signals from the acoustic emission sensor with the processor;
determining if the acquired signals correspond to a cavitation event having predefined characteristics;
recording selected characteristics of the acquired signals with the processor only if the acquired signals are produced by a cavitation event; and
determining the cavitation level from the recorded selected characteristics, the cavitation level being determined based on a rate of cavitation events and an intensity of each cavitation event.

13. The method of claim 12, wherein a cavitation event is defined by an acquired signal that is within a predefined filter range.

14. The method of claim 12, further comprising:
determining the rate of cavitation events by calculating a hit rate comprising the number of cavitation events that occur within a period of time; and
determining the intensity by calculating an energy unit per cavitation event.

15. The method of claim 12, wherein the flow control device comprises a control valve including a flow control member, the method further comprising:
determining a position of the flow control member;
comparing an expected cavitation level correlated to the position of the flow control member with the determined cavitation level; and
generating an alert if the expected cavitation level deviates from the determined cavitation level within a predefined level of significance.

16. The method of claim 12, wherein recording selected characteristics of the acquired signals comprises recording a voltage and threshold crossings of the acquired signals.

17. A method of monitoring an estimate of damage to a flow control device for process liquids caused by cavitation, wherein an acoustic emission sensor is coupled to an exterior wall of the flow control device and a processor is operatively coupled to the acoustic emission sensor to receive acoustic emission signals representative of transient acoustic energy data sensed in the fluid flow path by the acoustic emission sensor, the method comprising:
acquiring signals from the acoustic emission sensor with the digital signal processor, wherein the acquired signals are associated with transient acoustic emission data within a pre-defined range of frequencies;
recording selected characteristics of the acquired signals with the digital signal processor only if the acquired signals are produced by a cavitation event wherein the acquired signals are within a predefined filter range;

calculating, from the recorded selected characteristics, a hit rate comprising the number of cavitation events that occur within a selected period of time;

calculating, from the recorded selected characteristics, an intensity of each cavitation event, the intensity comprising an energy unit per cavitation event;

determining a cavitation level based on the hit rate and the intensity; and tracking an accumulation over time that the cavitation level exceeds a predetermined threshold, whereby an estimate of accumulated damage to the flow control device caused by cavitation may be monitored.

18. The method of claim 17, wherein the pre-defined range of frequencies is between about 500 kHz and about 1600 kHz.

19. The method of claim 17, wherein the characteristics of the acquired signals include at least one of a waveform of the acquired signal and an individual feature of the acquired signal.

20. The method of claim 17, wherein the step of determining comprises generating an alert only if the hit rate is greater than a predetermined hit rate threshold and the intensity is greater than a predetermined intensity threshold value.

21. The method of claim 20, wherein the step of tracking comprises incrementing a count in a counter in response to the alert to track a number of times the cavitation level exceeds the predetermined threshold, wherein the count is correlated with an estimation of damage to the flow control device.

22. The method of claim 20, wherein the step of tracking comprises tracking an accumulated amount of time that the cavitation level exceeds the predetermined threshold in response to the alert, wherein the accumulated amount of time is correlated with an estimation of damage to the flow control device.

23. A method of monitoring whether cavitation levels in a flow control device for process liquids are increasing, wherein an acoustic emission sensor is coupled to an exterior wall of the flow control device and a digital signal processor is operatively coupled to the acoustic emission sensor to receive acoustic emission signals representative of transient acoustic energy data sensed in the fluid flow path by the acoustic emission sensor, the method comprising:

acquiring signals from the acoustic emission sensor with the digital signal processor, wherein the acquired signals are generated in response to transient acoustic emission data within a pre-defined range of frequencies;

recording selected characteristics of the acquired signals with the digital signal processor only if the acquired signals are produced by a cavitation event wherein the acquired signals are within a predefined filter range;

calculating, from the recorded characteristics, a hit rate comprising the number of cavitation events that occur within a period of time;

calculating, from the recorded characteristics, an intensity of each cavitation event, the intensity comprising an energy unit per cavitation event;

calculating a trend of the hit rates and intensities with respect to time; and generating an alert that cavitation levels are increasing if the trend indicates that the hit rates and intensities are increasing over time.

24. The method of claim 23, wherein the alert is generated only if the trend shows that cavitation levels are increasing at a rate greater than a preselected rate within a preselected level of statistical significance.

* * * * *